United States Patent [19]

Loria et al.

[11] Patent Number: 5,407,684
[45] Date of Patent: Apr. 18, 1995

[54] USE OF DHEA AS A MEDICINAL

[75] Inventors: Roger M. Loria; William Regelson, both of Richmond, Va.

[73] Assignee: Virginia Commonwealth University, Richmond, Va.

[21] Appl. No.: 733,198

[22] Filed: Jul. 19, 1991

Related U.S. Application Data

[63] Continuation-in-part of Ser. No. 291,969, Dec. 30, 1988, Pat. No. 5,077,284.

[51] Int. Cl.⁶ .................... A23K 1/165; A01N 45/00; A61K 31/565; A61K 9/08
[52] U.S. Cl. .................. 424/442; 424/423; 424/439; 514/866; 514/885; 514/886; 514/909; 514/934
[58] Field of Search ............... 514/169, 178, 866, 885, 514/886, 909, 934; 424/422, 439, 442, 423

[56] References Cited

U.S. PATENT DOCUMENTS 4,518,595  5/1985  Coleman et al. ............. 514/178
4,956,355  9/1990  Prendergast ............. 514/99

Primary Examiner—Thurman K. Page
Assistant Examiner—Carlos Azpuru
Attorney, Agent, or Firm—Hendricks & Assoc.

[57] ABSTRACT

Dehydroepiandrosterone (DHEA) has an immune response regulating effect in vertebrates to protect from morbid effect of infection and immune suppressive therapies. DHEA is also effective for use in treatment of alopecia. Protection results from a generalized host response.

12 Claims, 2 Drawing Sheets

USE OF DHEA AS A MEDICINAL

This application is a continuation-in-part of application 07/291,969 filed Dec. 30, 1988, now U.S. Pat. No. 5,077,284.

SUMMARY OF THE INVENTION

The invention disclosed herein provides a means of regulating the immune response in vertebrates to protect from morbid effects of infection and immune suppressive chemotherapy and radiation therapy. DHEA is also useful for treatment of alopecia. Protection against morbidity arising from infection is not specific as to identity of the infectious organism, but is a generalized host response.

BACKGROUND OF THE INVENTION

In mammals the development of host protection against pathogens requires a selective host immune response that involves the mobilization of the humoral and/or cellular mediated immune responses. Several factors adversely affect the body's protective response capability by causing prolonged immune-suppression or "down-regulation" of the immune system associated with immune suppression is decreased resistance to infection. Immune-suppression provides an opportunity for pathogens to grow in the host. It does not matter what causes the primary insult to immunity. The resulting inability to muster the appropriate defensive response has the damaging effect of allowing organisms to grow and multiply in the host. Among the causes of immune-suppression are viral, bacterial, fungal, and parasitic infections, chemotherapy, irradiation, severe stress, and steroid therapy.

It has long been known some of the steroids of adrenocortical origin at pharmacologically appropriate doses cause patients to exhibit increased incidence of infectious disease. A. S. Fauci, *Immunolo. Rev.* 65, 133–155 (1982); and J. E. Parillo and A. S. Fauci, *Annual Review of Pharmacology and Toxicology* 19, 179–201 (1979).

Dehydroepiandrosterone, also known as 3-β-hydroxyandrost-5-en-17-one or dehydroiso-androsterone (referred to hereinafter as DHEA), is a 17-ketosteroid which is quantitatively one of the major adrenocortical steroid hormones found in mammals. M. E. Windholz, *The Merck Index*, Ninth Edition (1976); K. Diem and C. Lentner, *Geigy Scientific Tables* (1975). Although DHEA appears to serve as an intermediary in gonadal steroid synthesis, the primary physiological function of DHEA has not been fully understood. It has been known, however, that levels of this hormone begin to decline in the second decade of life, reaching 5% of the original level in the elderly.

Clinically, DHEA has been used systemically and/or topically for treating patients suffering from psoriasis, gout, and hyperlipemia. It has also been administered to post-coronary patients. (W. Regelson et al., *New York Academy of Sciences* 518, 260–273 (1988).) In mammals DHEA has been shown to have anti-obesity and anti-carcinogenic effects.

DHEA has been used clinically in Europe in conjunction with estrogen as an agent to reverse menopausal symptoms and also has been used in the treatment of manic depression, schizophrenia, and Alzheimer's disease. DHEA has also been used clinically at 40 mg/kg/day in the treatment of advanced cancer and multiple sclerosis. Regelson, supra. Mild androgenic effects are often associated with administration of DHEA. These side effects can be overcome by monitoring the dose and/or by using analogues.

BRIEF DESCRIPTION OF THE DRAWINGS

FIG. 1(a) compares mortality in male mice that had been injected intraperitoneally with Coxsackievirus B4 (CVB4) or with CVB4 and DHEA.

FIG. 1(b) compares mortality in female mice injected intracranially with HSV2 or with HSV2 and DHEA

FIG. 2(a) compares mortality in mice given coxsackievirus with mortality in mice given coxsackievirus and DHEA.

FIG. 2(b) compares mortality in mice given herpes virus type 2 with mortality in mice given herpes virus type 2 and DHEA morality.

FIG. 4(a) compares IgM AFC spleen cells.

FIG. 4(b) compares IgG AFC spleen cells.

DESCRIPTION OF THE INVENTION

Figure 1A:
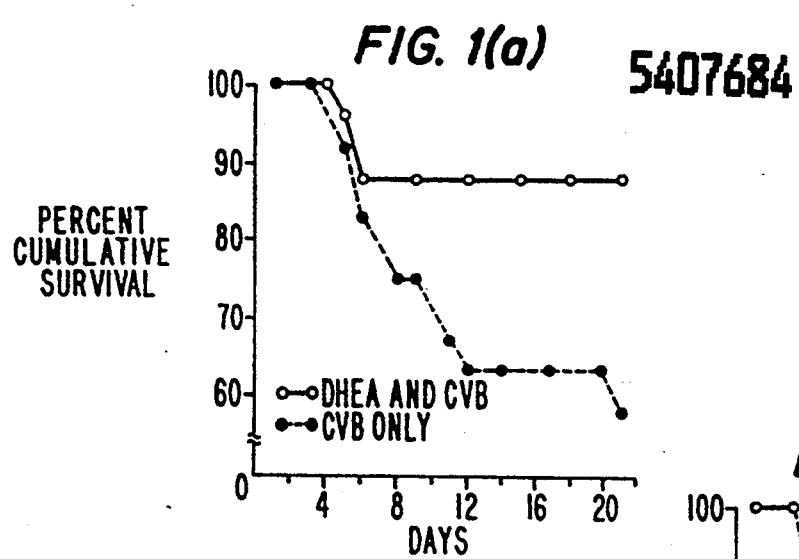
FIGS. 1(a) and 1(b) show graphs illustrating the effect of DHEA on survival of C57BL/6J mice following virus injection.

The use of DHEA as taught herein provides high levels of protection to vertebrates, including humans, against morbidity arising from infections. In clinical medicine, treatment with DHEA can lower morbidity in patients exposed to pathogenic organisms. It can be effectively used in patients known to be particularly susceptible to infection. Patients undergoing surgery or chemotherapy or patients suffering from burns, hypoplastic or aplastic anemias, or diabetes are such susceptible patients who would benefit from prophylactic administration of DHEA. DHEA is particularly useful for treating patients suffering from infections caused by viruses that destroy the body's immune response, such as Human Immunodeficiency Virus (HIV).

DHEA can also be used in veterinary medicine to prevent morbidity that occurs during stress of shipping. Administration of DHEA can be used to prevent spread of infectious disease and introduction of infectious organisms into the foods for human consumption. DHEA can be administered in food or drink or by patches applied to the skin. A particular concern is the spread of infection through eggs. Eggs are frequently infected during development in the hen. DHEA may be added to the feed or water to prevent bacterial infection in the eggs.

DHEA may also be given with vaccines to enhance immune response. It may be administered either in a composition containing in combination the vaccine and DHEA or it may be given in a composition separate from the vaccine.

The pharmaceutical compositions used for purposes taught herein are administered in a manner that will result in contact of the active agent with tissues of ectodermal origin. DHEA may be delivered to the cutaneous tissue by any means including subcutaneous or intradermal injection or by topical application. One means of topical application is the use of skin patches impregnated with DHEA. This means of delivery is advantageous since it is non-invasive and is easily administered by relatively unskilled care providers.

Some other preferred methods of administration include buccal, nasal or endotracheal routes. Sprays may be useful for this purpose. For nasal administration, the active agent may be delivered as a powder that is snorted. Inclusion complexes such as cyclodextrin inclusion complexes are appropriate compositions and would be particularly useful for buccal administration of these active agents.

The compounds of the invention may also be administered to the intestinal mucosa by oral or rectal routes. Suppositories, solutions for use as retention enemas, and creams or jellies are appropriate carriers for use in rectal administration.

Compounds of the invention may be applied to the vaginal mucosa using creams, jellies, suppositories, or douching solutions.

In order to enhance immune response at the site of exposure to infectious organisms, the compounds may be added to prophylactic vaginal preparations or may be used as lubricants on condoms.

Administration of compositions of the invention intracranially has proven to be highly effective as a means of protecting against encephalitis and meningitis. The compositions of the invention may be administered intrathecally either at the spinal level or into the cisterna magna.

DHEA may be administered via ocular route using compositions such as drops, creams, or gel suspensions adapted for ocular application.

The active agents of the invention may be delivered directly to the epithelial tissue during surgery. An example of such use would involve the application of compositions containing the active agents of the invention to the omentum in conditions such as endometritis and malignancies of the bowel and ovary. Compositions of the invention could, for example, be administered as mists or sprays.

It is particularly important to note that the DHEA and its analogues can be administered in food or drink. While the higher dosage levels are required when DHEA is given in food or water, these compositions are particularly manageable for administration in commercial settings to protect birds, mammals, or fish. The active agents may be administered in baits to increase selective ingestion.

Dosage requirements will depend on the route of administration and the size of the vertebrate since smaller animals with higher metabolism require much higher dosages. In small animals preferred dosage would be 0.01 gm-1 gm/kg/da. In a mammal as large as man, dosage of as little as 0.05 mg/kg/da to 2 mg/kg/da could be effective, depending on the age, size, and condition of the patient.

Two acute virus infection models were examined to determine the effects of DHEA on virus-mediated pathophysiology. Coxsackie-virus B4 (CVB4) is a virus that is lethal to mice. (In man Coxsackie viruses cause such varied pathologies as upper respiratory infection, pharyngitis, hemorrhagic conjunctivitis, meningitis, exanthem, encephalitis, hepatitis, infantile diarrhea, paralysis, pericarditis, and myocarditis. It is now believed that viruses of this group also have a role in the onset of juvenile diabetes. Herpes simplex type 2 (HSV2) causes primary and recurrent genital inflammation. However, in the newborn meningoencephalitis often seen, and can result in death or severe complications. Male mice have been have been shown to be more susceptible than female mice to CVB4, while female mice have been shown to be more susceptible to infection with HSV2. Therefore, male inbred C57BL/6J mice 6 to 8 weeks old (Jackson Laboratories, Bar Harbor, Me.) were infected with CVB4. Female mice of the same age and strain were used for tests wherein the animals were infected with HSV2 injected intracranially.

Unless indicated otherwise, animals used were maintained on normal laboratory mouse chow. In experiments where animals were maintained on a semipurified diet high in animal fat, the diet contained 20% casein, 52.5% sucrose, 18% animal fat (lard), 5% cellulose, 4% salts, 0.2% choline chloride, 0.1% inositol and 0.1% vitamin mix.

EXAMPLE 1

Male mice were given DHEA in DMSO by subcutaneous injection before being infected with CVB4 by intraperitoneal route. Controls were also infected with CVB4 in the same manner after subcutaneous injection of DMSO. Dose of CVB4 ranged from $10^2$ PFU/animal to $10^5$ PFU/animal.

Ten days after CBV4 infection, test and control animals were immunized by intraperitoneal injection with $5 \times 10^8$ sheep red blood cells (SRBC). Four days after SRBC immunization, the animals were killed with an overdose of anesthetic and the spleen was removed. (See E. Moller, et al, Eur. J. Immunol. 3, 172–179 (1973) for the enumeration of spleen cells secreting IgM-antibody.)

Peripheral white blood cells from the animals were counted following Diff-Quik (American Scientific Products, McGraw Park, Ill.) staining of blood smear. No differentiation of lymphocytes or monocytes by special stains or cell marker was done.

For histopathological studies, animals were sacrificed using an overdose of methoxyflurane (Metofan, Pitman-Moore, Inc., Washington Crossing, N.J.); tissues were removed and fixed in phosphate-buffered formaldehyde at room temperature. Specimens were embedded in paraffin, sectioned and stained with hematoxylin and eosin.

EXAMPLE 2

Female mice were given DHEA in DMSO by subcutaneous injection followed by challenge with HSV2 administered by intracranial injection of the virus. Controls were challenged with intracranial injections of HSV2 in the same manner using DMSO in place of DHEA.

Figure 1B:
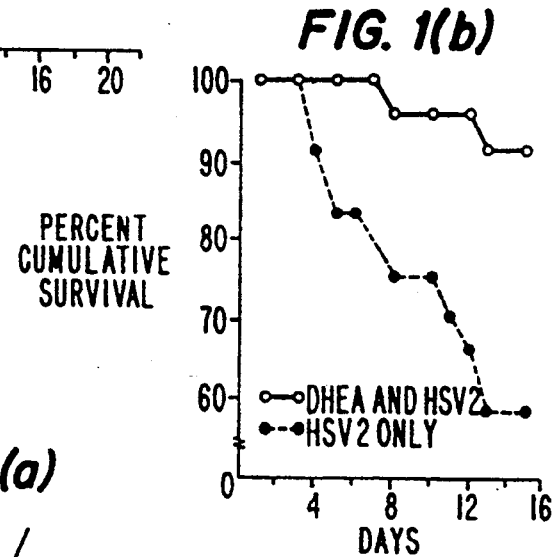
Figure 2A:
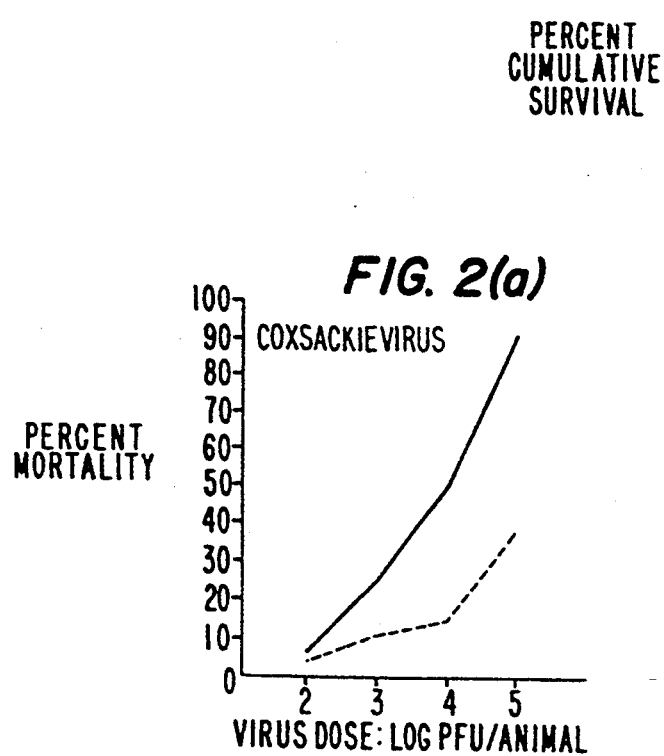
FIGS. 2(a) and 2(b) are a pair of graphs illustrating effects of DHEA injection on response to virus.
Figure 2B:
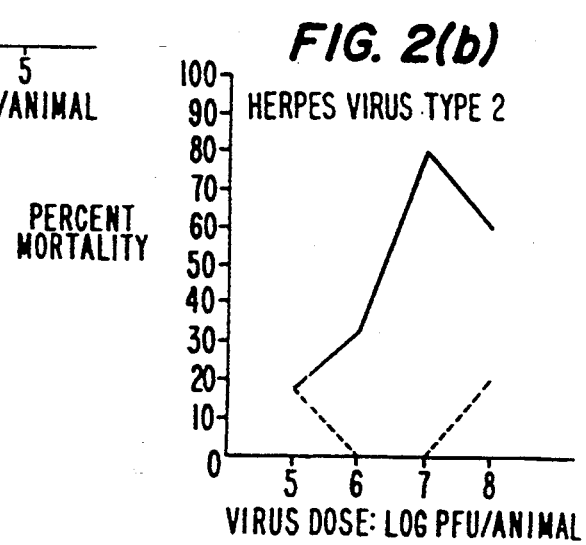

The protective effects of 25 mg DHEA injected subcutaneously on the survival of animals challenged with CVB4 and HSV-2 are indicated in FIGS. 1a and 1b, respectively. The results show that the percent cumulative survival of animals following CVB4 infection was close to 90% in DHEA-treated mice as compared to about 58% in control animals. An almost identical increase in cumulative survival was achieved in DHEA-treated mice when challenged with HSV2.

Figure 4A:
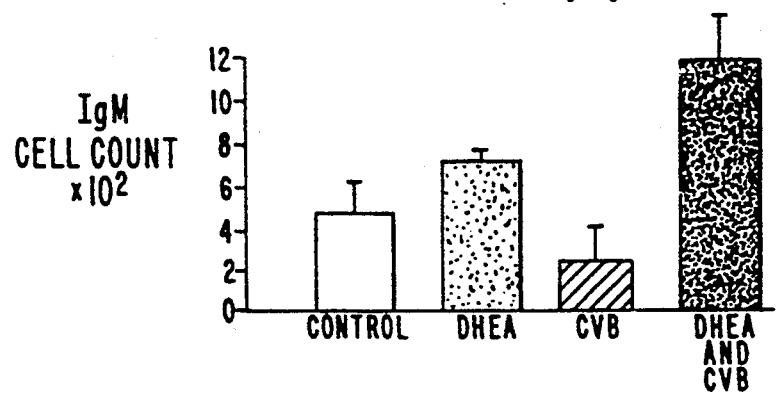
FIGS. 4(a) and 4(b) illustrate the effect of DHEA on the number of spleen antibody forming cells (AFC).
Figure 4B:
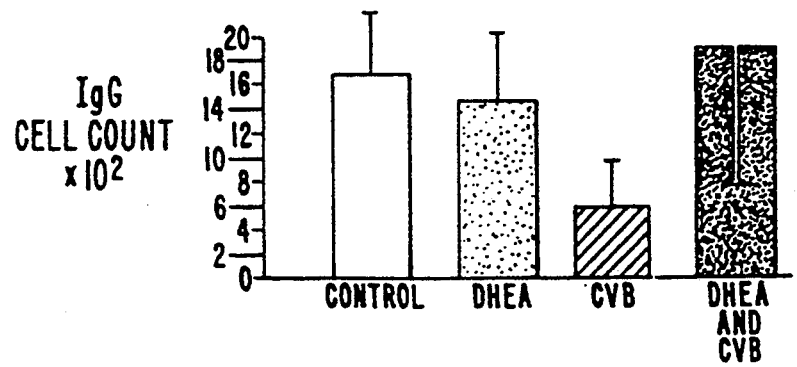

The effect of DHEA on number of spleen antibody-forming cells (AFC) in virus-infected and uninfected animals was determined by sheep red cell immunization as described in Example 1. The number of IgM AFC per $10^6$ spleen cells in uninfected and CVB4-infected mice with and without DHEA treatment were counted. (See FIG. 4a). The number of IgM AFC per $10^6$ spleen cells was 35% higher in uninfected DHEA-treated mice than in uninfected control mice. The increase was not deemed statistically significant. However, in CVB4-infected DHEA-treated mice the number of spleen IgM AFC was 80% higher than the number of IgM AFC in CVB4-infected control mice ($P \leq 0.025$). The number of spleen IgG AFC was also enumerated (FIG. 4b).

Histopathological studies of hematoxylin and eosin stained spleen sections revealed that the spleen periarteriolar sheath of lymphocytes (PALS), which is composed largely of T lymphocytes that are primarily Thy 1.2 cells, were well developed in both DHEA-protected animals infected with CVB4 and in unprotected CVB4-infected animals. However, infection with CVB4 in the unprotected animals was associated with reduction in the number and size of spleen germinal centers. In contrast, in DHEA-treated animals there was a marked increase in the number and size of splenic germinal centers suggesting B lymphocyte hyperplasia and a marked increase in the hematopoietic activity in the spleen red pulp. Furthermore in the unprotected CVB4 infected animals the spleen white pulp was characterized by a prominent "starry sky" pattern indicative of phagocytosis of a large number of dead lymphocytes. In DHEA protected animals, the "starry sky" pathological pattern was reduced.

The effect of DHEA on peripheral leukocyte concentrations was also evaluated in the following groups: (1) control (no DHEA, no viral challenge), (2) DHEA given subcutaneously at dosage of 1 g/kg, no viral challenge, (3) CVB4 infection without DHEA protection, and (4) 1 g/kg DHEA (subcutaneous) injection followed by CVB4 challenge. Review of data showed no significant effect from administration DHEA alone on the total leukocyte count when compared with untreated, noninfected animals. The total leukocyte count 3 days after infection was significantly lower in DHEA-treated/CVB4-infected animals than in all uninfected animals whether or not they had been given DHEA. The monocyte counts three days after infection of the DHEA treated mice showed 84.5% lower count while the infected mice denied DHEA showed 50% lower count when compared with uninfected controls. However, 7 days after infection the DHEA-treated, CVB4-infected group showed a monocyte count 214% higher than the virus-infected animals who had received no DHEA. In uninfected animals, DHEA-treated animals showed only a 62% increase in monocyte count over control animals. It is, therefore, shown that (1) DHEA causes a selective stimulation of leukocyte proliferation in the presence of an immunogen and (2) the action is biphasic, that is, the initial reaction is one of decreased leukocyte proliferation followed by greatly increased leukocyte proliferation.

Figure 3:
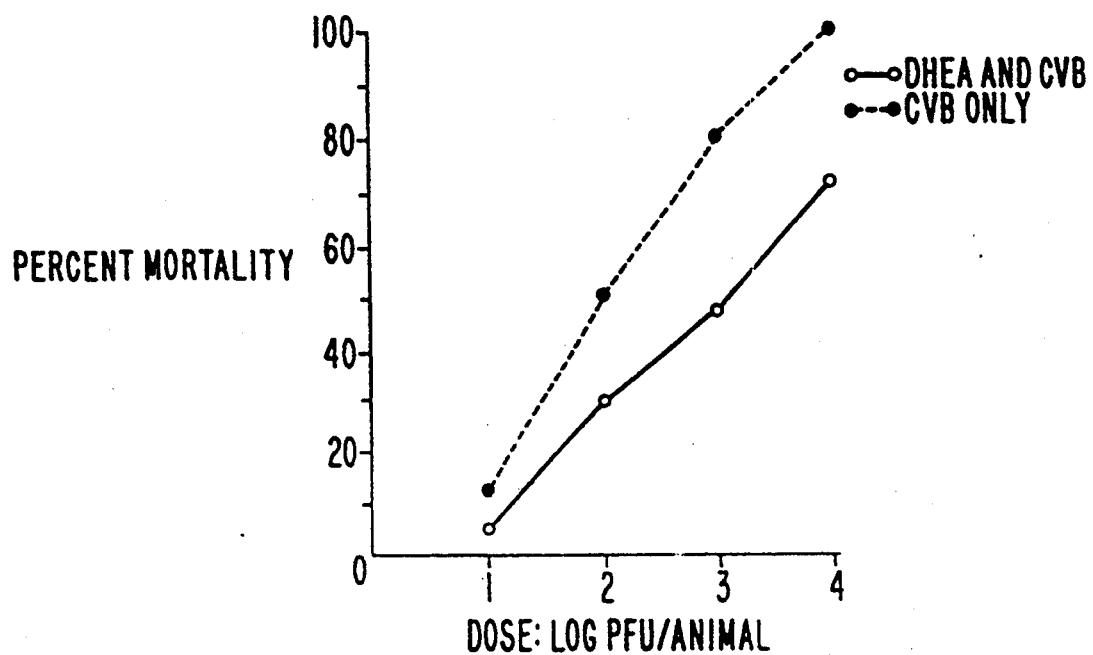
FIG. 3 is a graph illustrating the effects of feeding animals a diet containing 0.4% DHEA on response of mice to CVB4 virus injections.

Prolonged feeding of a diet containing 0.4% DHEA also provided protective effect against morbidity in CVB4 infected animals. (See FIG. 3.) However, the protection against lethal virus infection following subcutaneous injection of DHEA was achieved at lower dosage than the dosage required to achieve similar results when DHEA was fed in the diet.

In vitro experiments were done to determine whether DHEA had any direct effect of CVB4 infectivity and replication. HeLa cells in culture were incubated with either 2 $\mu M$ or 20 $\mu M$ DHEA and inoculated with 100 PFU CVB4. No evidence of a reduction in the number of CVB4 plaque-forming units could be detected at these concentrations of DHEA.

It is known that one of the common results of chemotherapy and radiation therapy is alopecia. Alopecia is also seen in pathologies that attack the immune system such as HIV infection and leukemias. Systemic administration of DHEA is useful for treatment of alopecia through regulation of the immune system. The hr/hr strain of mice, a hairless breed which genetically lacks capability to raise an immune response, neither develops improved protection against infection nor hair when given DHEA. However, the nu/nu strain of mice commonly called "nude", a hair-deficient breed which has a defective immune system, grows hair in response to administration of DHEA. Hence, a defective immune system can be upregulated by administration of DHEA. However, when an immune system is genetically lacking no response to DHEA is seen.

It is known that coxsackieviruses, like other viruses that reduce the broad immune response, render the host susceptible to other infecting organisms. Many of the deaths associated with such viruses that severely damage the immune system result from secondary opportunistic infections such as bacterial or fungus infections because the host is unable to raise an appropriate response to the infections. Two individuals diagnosed as having AIDS or AIDS Related Complex (ARC) were treated with oral doses of DHEA. A summary of results follows.

EXAMPLE 3

A 28 year old caucasian male, an active homosexual with ARC had had an affair with a man who died of AIDS. He had been well until January, 1986,when he developed "cold sores" in his mouth followed by fever and diarrhea. Chest X-rays findings were consistent with a diagnosis of Pneumocystis Carinii Pneumonia. Laboratory findings: HTLV-III positive, Pneumocystis Carinii culture positive, severe thrombocytopenia.

On Nov. 11, 1986 oral treatment with 400 mg/day of DHEA was initiated. By Feb. 8, 1987 the patient had gained 14 pounds.

EXAMPLE 4

A white male with factor VIII deficiency hemophilia was found to be HTLV-III positive. The AIDS manifested as "hepatitis" and lymphadenopathy. The number of T4 lymphocytes was low and DHEA levels were normal. Treatment with DHEA 40 mg/kg/d given in 4 oral doses was begun. The patient showed weight gain and return of appetite following treatment with considerable improvement in lymphadenopathy. (The patient later died from malignancy of the liver.)

DHEA is a lipophilic compound. Solvents for lipophilic steroids are known in the art and would be used as carriers. Examples of such carriers include glycols such as polypropylene glycol and polyethylene glycol. Cyclodextrins, especially the intrinsically amorphous cyclodextrins, would be appropriate carriers. Other vehicles that may be used include fatty acid esters of polyoxyethylene sorbatan (Tweens) or sorbitan (Spans) to prepare oil-in-water emulsions.

While the use of DHEA in feed resulted in up-regulation of the immune system, the amount of active agent administered was much larger than was required when DHEA was given by injection. DHEA is most effective when the period of exposure to the mucosa of the intestine is increased. Hence, use of capsules containing the DHEA that effect slow release in the intestine is appropriate. The capsules may be placed in baits for administration to animals. Use of retention enemas for treatment of infections of the large bowel is also deemed appropriate.

DHEA may be administered to the mucosa of the oral cavity as a buccal tablet or may be administered as a spray for use in the oral-pharyngeal cavity or as a nasal spray.

Compositions can be administered to the bronchial tree via inhalation therapy. This means of administration would be particularly useful in treating patients with lung infections to up-grade local immune response.

Administration to the skin can be accomplished using patches wherein a support to be applied to the skin is impregnated with the active agent. If the DHEA is given to an animal, it may be necessary to shave the region.

DHEA can be used as an adjunct in vaccination to increase response to an immunogen. Such use is particularly appropriate in instances where inhibition of immune response can be a complicating factor as is the case in patients suffering from, for example, malignancies, AIDS, or environmental factors such as exposure to pesticides. It is, of course, understood that use as adjunct to vaccination would be appropriate in vertebrates other than man, including vaccination of pets, dairy animals, meat-producing animals, fish and chickens.

Chickens are particularly prone to develop infectious diseases when living in confined conditions. Coccidiosis, Salmonella infections, and viral infections, including those giving rise to malignancies such as leukemia and sarcoma (caused by a retrovirus) are particularly common among chickens grown under modern commercial conditions. DHEA can be added to water or feed to improve protective immune response to microbial assault.

The effect of Coxsackie virus and Herpes virus on humans has been noted previously. Effects of chickenpox-herpes zoster is also considered important since herpes zoster is a common cause of debilitating illness in the elderly. Furthermore, chickenpox in the susceptible adult often causes sever illness. In children chickenpox can cause death when the child has been subjected to immuno suppressive therapy or is genetically immune deficient. DHEA should be considered as a prophylactic for treatment of susceptible adults that have been exposed to infection. While HSV2 is often painful in the adult, exposure to the virus either prenatally or during birth can often lead to death in the newborn. Use of DHEA during the third trimester in infected woman may be considered as a means of protecting the newborn.

DHEA may be administered as a prophylactic during irradiation therapy or chemotherapy or after exposure to irradiation whether the exposure occurs as a result of environmental accident or therapy. The compositions of the invention are useful for alleviation of alopecia, a distressing side effect of such therapies.

As previously indicated, administration of DHEA is appropriate to effect improved function of the immune system are during treatment of patients with burns, hypoplastic and aplastic anemias, diabetes, and in the elderly during epidemics. Even after symptoms of infectious disease are evident, use of DHEA is beneficial to mitigate effects of exposure to infectious organisms. DHEA may also be administered before "dirty" procedures such as dental work, oral surgery, or bowel resection to improve protective function of the immune system.

Dosage will differ with the species. In humans, dosage of as little as 1 mg to 100 mg per day is sometimes effective. Exact dosage will depend on the age, size, and condition of the patient. Dosage of 10 to 100 mg per day is suggested for human patients with untoward response to irradiation and chemotherapy and for patients suffering from alopecia from any cause. In AIDS and leukemia patients dosages of up to 1000 mg may be required. Smaller vertebrates require higher dosage. In treating chickens using injection a dose of 10 mg/kg to 1000 mg/kg should be considered. Higher dosage will be required if the DHEA is administered in the feed.

I claim:

1. A method of enhancing protective immune response by administration of 1 to 1000 mg per day of DHEA to a mammal in need of enhancing of the protective immune response.

2. A method of claim 1 wherein the mammal has been exposed to radiation or chemotherapy.

3. A method of claim 1 wherein the DHEA is given as an adjunct to a vaccine.

4. A method of claim 1 wherein the mammal is a farm animal.

5. A method of claim 4 wherein the DHEA is administered to the mammal in feed or water.

6. A method of claim 1 wherein the mammal is a human suffering from anemia.

7. A method of claim 1 wherein the mammal is a human who suffers from burns.

8. A method of claim 1 wherein the mammal is a human suffering from diabetes.

9. A composition of matter comprising fish or bird food or water containing DHEA.

10. A composition of matter comprising an immune-enhancing amount of DHEA and a vaccine in a pharmaceutically acceptable carrier.

11. A method of enhancing protective immune response of a fish or bird by administration of an immune enhancing effective amount of a composition of claim 1.

12. A method of claim 1 wherein the mammal is a human suffering from herpes simplex.

* * * * *